(12) United States Patent
Nord et al.

(10) Patent No.: US 7,839,973 B2
(45) Date of Patent: Nov. 23, 2010

(54) TREATMENT PLANNING USING MODULABILITY AND VISIBILITY FACTORS

(75) Inventors: Janne Nord, Espoo (FI); Jarkko Peltola, Tuusula (FI); Lasse Toimela, Baden-Daettwil (CH)

(73) Assignee: Varian Medical Systems International AG (CH)

( * ) Notice: Subject to any disclaimer, the term of this patent is extended or adjusted under 35 U.S.C. 154(b) by 0 days.

(21) Appl. No.: 12/353,744

(22) Filed: Jan. 14, 2009

(65) Prior Publication Data
US 2010/0177870 A1  Jul. 15, 2010

(51) Int. Cl.
*A61N 5/10* (2006.01)
(52) U.S. Cl. .......................................... 378/65
(58) Field of Classification Search ............ 378/62, 378/64, 65, 68
See application file for complete search history.

(56) References Cited

U.S. PATENT DOCUMENTS

2009/0003523 A1 *  1/2009  Raanes et al. ................. 378/65

\* cited by examiner

*Primary Examiner*—Irakli Kiknadze
(74) *Attorney, Agent, or Firm*—Vista IP Law Group, LLP.

(57) ABSTRACT

A method for use in a treatment planning process includes determining a modulability factor, and determining a treatment parameter using the modulability factor. A system for use in a treatment planning process includes a processor, wherein the processor is configured for determining a modulability factor, and determining a treatment parameter using the modulability factor. A method for use in a treatment planning process includes determining a visibility factor, and determining a treatment parameter using the visibility factor. A system for use in a treatment planning process includes a processor, wherein the processor is configured for determining a visibility factor, and determining a treatment parameter using the visibility factor.

38 Claims, 5 Drawing Sheets

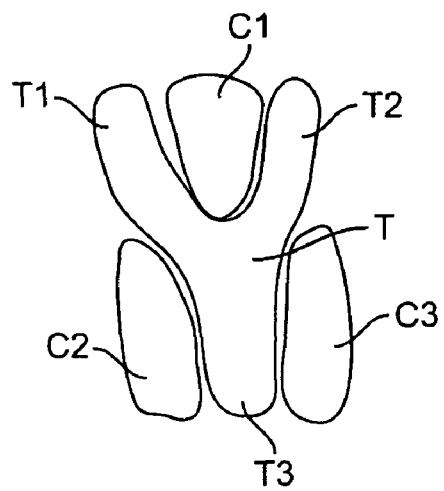
FIG. 4A
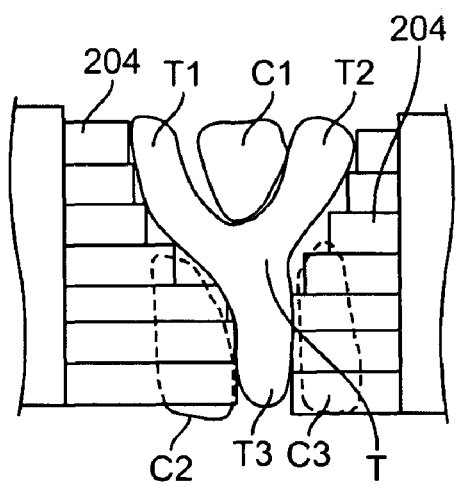
FIG. 4B
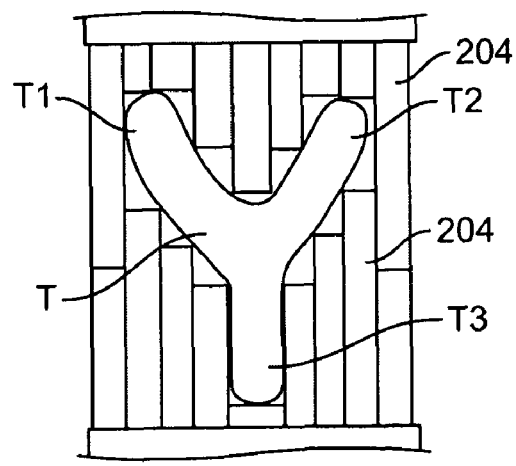
FIG. 4C
```
C  T  C  T  C
C  T  C  T  C
T  C  T  C  T
T  C  T  C  T
T  C  T  C  T
```
FIG. 4D

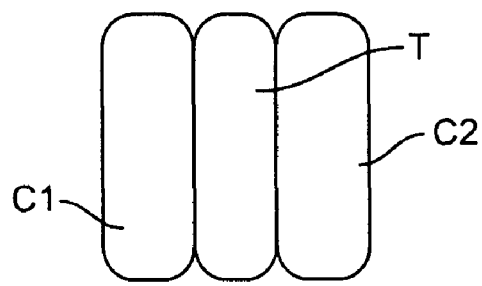
FIG. 5A
```
C  C  T  C  C
C  C  T  C  C
C  C  T  C  C
C  C  T  C  C
```
FIG. 5D
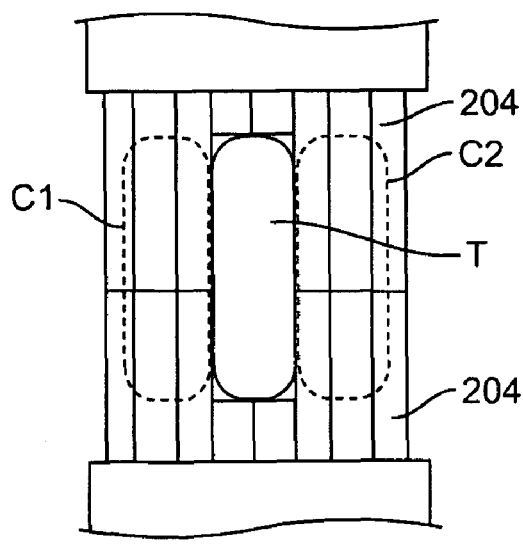
FIG. 5B
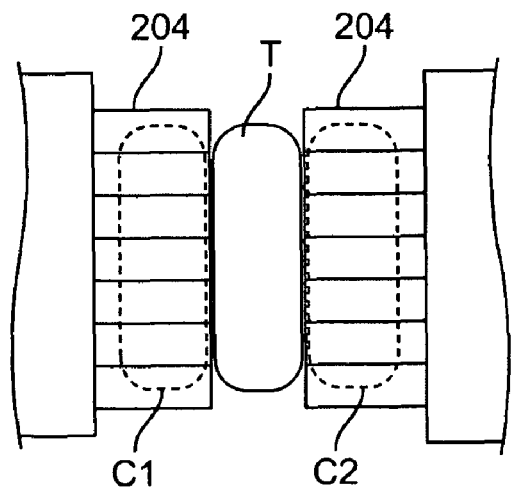
FIG. 5C

TREATMENT PLANNING USING MODULABILITY AND VISIBILITY FACTORS

FIELD

This application relates generally to radiation therapy, and more specifically, to radiation treatment planning.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Generally, a radiation treatment plan is determined before the radiation therapy is performed. During a radiation planning session, radiation treatment planning is performed before treatment radiation is delivered to a patient. This allows an accurate and precise dosage of radiation to be delivered to a patient. During a radiation treatment planning, geometry parameters, such as isocenter position, rotation axis, and collimator angle are determined. In existing techniques, these geometry parameters are set manually. However, in many cases, it may be difficult to manually choose these parameters in arc therapy so that good results are obtained from the treatment planning optimization. This is because isocenter position, rotation axis, collimator angle, and other parameters affect arc therapy plan quality in a complex way.

SUMMARY

In accordance with some embodiments, a method for use in a treatment planning process includes determining a modulability factor, and determining a treatment parameter using the modulability factor.

In accordance with other embodiments, a system for use in a treatment planning process includes a processor, wherein the processor is configured for determining a modulability factor, and determining a treatment parameter using the modulability factor.

In accordance with other embodiments, a method for use in a treatment planning process includes determining a visibility factor, and determining a treatment parameter using the visibility factor.

In accordance with other embodiments, a system for use in a treatment planning process includes a processor, wherein the processor is configured for determining a visibility factor, and determining a treatment parameter using the visibility factor.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 4A illustrates an example of a target next to critical organ;

FIG. 4B illustrates an example of a collimator shaping a beam in one configuration to conform with the target of FIG. 4A;

FIG. 4C illustrates an example of a collimator shaping a beam in another configuration to conform with the target of FIG. 4A;

FIG. 4D illustrates a model for the example of the target and critical organ shown in FIG. 4A;

FIG. 5A illustrates another example of a target next to critical organ;

FIG. 5B illustrates an example of a collimator shaping a beam in one configuration to conform with the target of FIG. 5A;

FIG. 5C illustrates an example of a collimator shaping a beam in another configuration to conform with the target of FIG. 5A;

FIG. 5D illustrates a model for the example of the target and critical organ shown in FIG. 5A.

DESCRIPTION OF THE EMBODIMENTS

Figure 1:
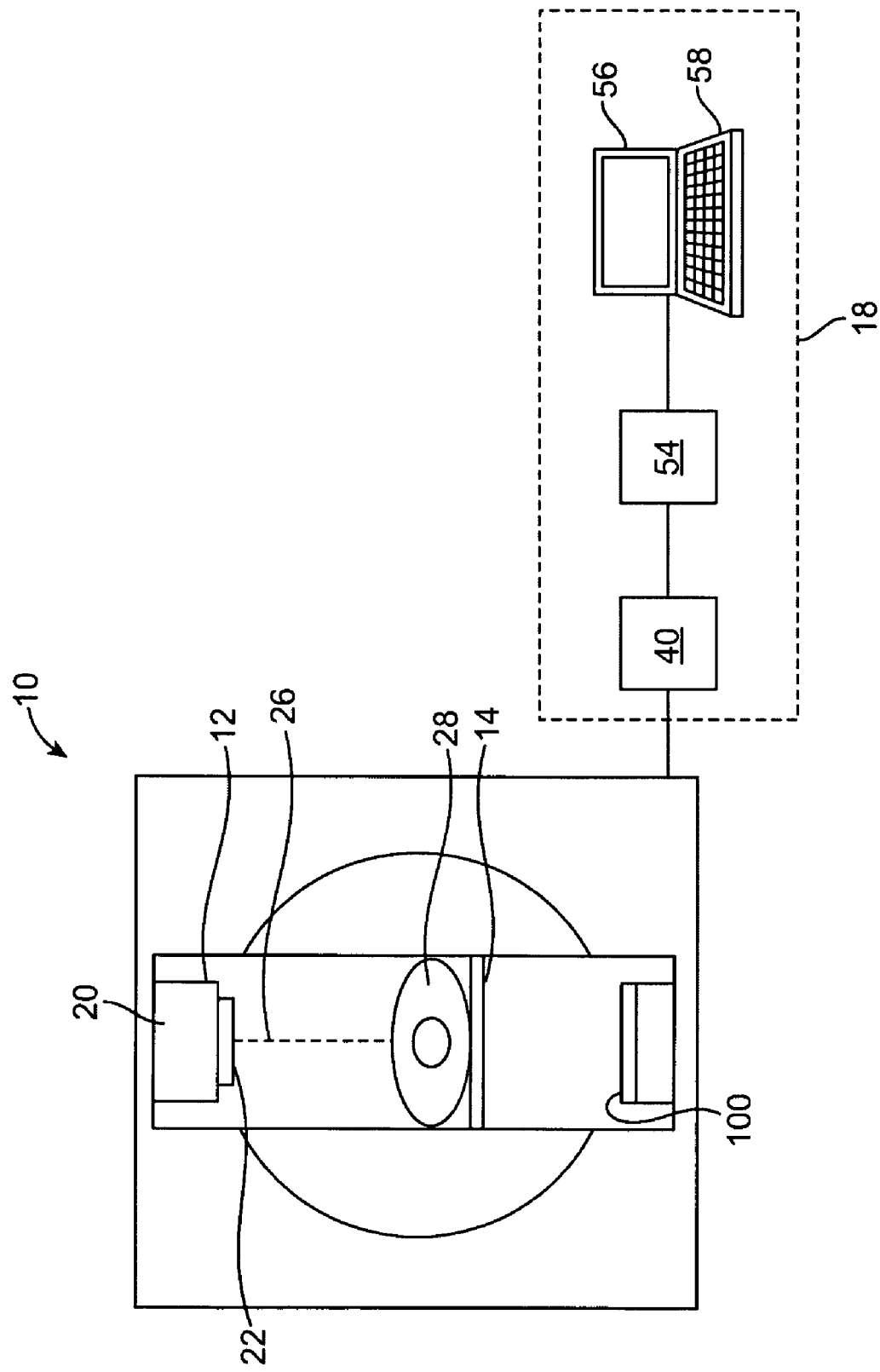
FIG. 1 illustrates a system for delivering radiation in accordance with a treatment plan determined in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. The system 10 includes a gantry 12 (in the form of an arm), a patient support 14 for supporting a patient, and a control system 18 for controlling an operation of the gantry 12. The system 10 also includes a radiation source 20 that projects a beam 26 of radiation towards a patient 28 while the patient 28 is supported on support 14, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source 20 can be a diagnostic radiation source. In the illustrated embodiments, the radiation source 20 is coupled to the arm gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arc-therapy). In other embodiments, the gantry 12 does not rotate about the patient 16 during a treatment procedure. In such case, the gantry 12 may be fixed, and the patient support 14 is rotatable. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. Further, the radiation source 20 is not limited to delivering treatment energy in the form of x-ray, and may deliver other types of radiation energy. For example, in other embodiments, the radiation source 20 may be a proton source for delivering protons to treat patient, or other types of particle source for delivering other types of particles for treating patient.

Figure 2:
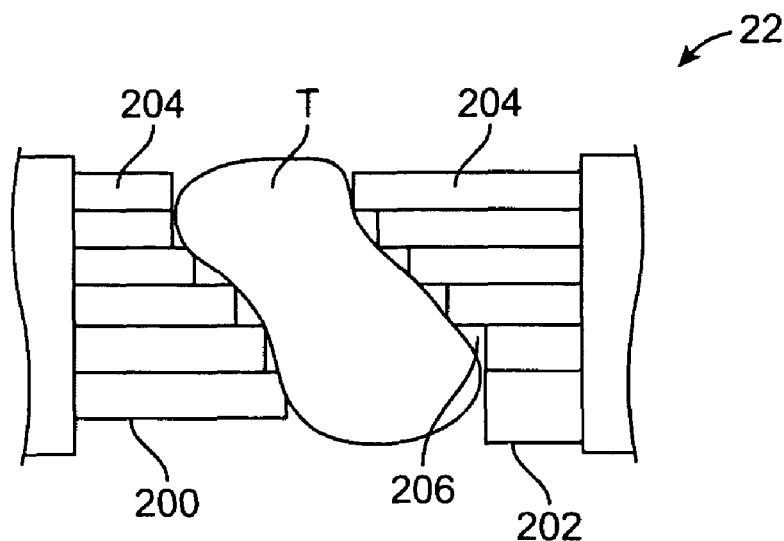
FIG. 2 illustrates a multi-leaf collimator shaping a beam to conform with a target.

In the illustrated embodiments, the collimator system 22 is a multi-leaf collimator that includes a plurality of leaves. FIG. 2 illustrates an example of the collimator system 22 of FIG. 1 that includes two opposing sets 200, 202 of leaves 204. As shown in the figure, the collimator 22 has been configured to create an aperture 206 having a shape that conforms with a target T. During use, the collimator 22 is operated to created different shapes to conform with the target T as the gantry 12 is rotated at least partially about the target T. In some embodiments, if the target T moves during a treatment process, the collimator 22 can also be operated to move the leaves to track the movement of the target T. In further embodiments, the collimator 22 can be operated to modulate an intensity of a radiation being delivered to the target T. For example, the leaves may be positioned to create a first aperture for delivering radiation to the entire target T for a given duration. Some of the leaves may then be positioned again to block off radiation being delivered to part(s) of the target T. As a result, different parts of the same target T may receive different amount of radiation dose. The intensity modulation by the collimator 22 may be performed for target T that is stationary, or for target T that moves, in which case, the intensity modulation is performed in conjunction with tracking the target T.

Figure 3:
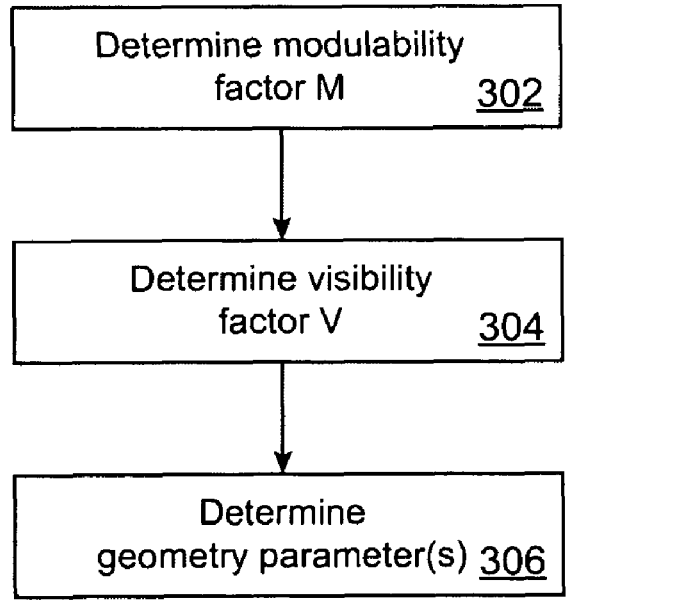
FIG. 3 illustrates a method for use in a treatment planning process in accordance with some embodiments.

FIG. 3 illustrates a method 300 for determining one or more geometry parameters in accordance with some embodiments. As used in this specification, the term "geometry parameter" may be one or more parameters that represent a configuration or a feature of a machine or a patient setup. By means of non-limiting examples, the geometry parameter may be one or a combination of an isocenter position, a rotation axis, a collimator position (e.g., collimator angle, such as that about a beam axis), and a patient support position (which corresponds with a patient position, e.g., location, orientation), etc. The geometry parameter(s) may be used and/or incorporated in a treatment plan and form part(s) of the treatment plan. Thus, the method 300 may be for use in a treatment planning session (e.g., for arc therapy, which may or may not involve intensity modulated radiation therapy (IMRT)), and the geometry parameter(s) may be considered treatment parameter(s) themselves. In some embodiments, the method 300 may be used to optimize geometry parameter(s) in arc therapy for one or more arc fields.

First, a modulability factor M is determined (Step 302). The modulability factor represents (and therefore, may be used to measure) a system's ability to modulate (e.g., adjust) its components to achieve a desired configuration. For example, the modulability factor may be used to measure a collimator's ability to modulate its leaves to achieve a given shape of a target in some embodiments. In some embodiments, the modulability factor may be based on a number of leaves participating, a measure of how independent (weakly coupled) the dose to a given subvolume is from that of other subvolume(s), and/or other factor(s), as described in further details below. The modulability factor may be a variable, a value, a matrix, or a function. In some embodiments, the modulability factor M is determined by the processor 54 receiving an input (e.g., from a user or a communication device) regarding the modulability factor M. In other embodiments, the modulability factor M is determined by the processor 54 executing a program that involves initializing and/or using the modulability factor M.

The concept of the modulability factor M is illustrated in FIGS. 4A-4D. FIG. 4A with respect to the collimator 22, which is for use to deliver a fluence towards a target T next to critical organ C. Fluence is the amount of radiation passing through a spatial region, and may be represented by a fluence map. A fluence map is a matrix that covers a spatial region (e.g., a plane). For each point in the plane, the fluence map defines the amount of radiation passing through that element. The target T includes target regions T1, T2, T3 (each of which may be considered a target itself). The critical organ C includes critical region C1, C2, C3 (each of which may be considered a critical organ itself). FIG. 4B illustrates an example of a collimator's configuration for providing a fluence that conforms with the target T to some degree. In the illustrated example, the collimator 22 is oriented left-to-right, with the leaves 204 positionable in a left-right direction. As a result, the shape of the target T3 can be fully realized by leaves 204. However, the shapes of targets T1, T2 cannot be fully achieved by the leaves 204 (i.e., a single configuration of the leaves) because there is a critical organ C1 in between T1 and T2. FIG. 4C illustrates another example of a collimator's configuration for providing a fluence that conforms with the target T. In the illustrated example, the collimator 22 is rotated 90° (relative to the beam axis) relative to the position of FIG. 4B, and is oriented up-and-down, with the leaves 204 positionable in an up-down direction. As a result of the orientation of the collimator 22, the shapes of targets T1-T3 can be fully achieved. As illustrated in the above example, if the leaves are oriented in a certain direction, it may not be possible to irradiate only target, and by changing an orientation of the collimator, it is possible to irradiate only target (or more of the target, or less of the critical organ). In the example shown in FIG. 4C, the leaves can let radiation pass in one continuous segment to reach only targets T1-T3. So the continuous segments should align with projections for the targets T1-T3.

In some embodiments, the modulability factor M may be based on a calculation of the size of longest target segment for each leaf 204. In this case, the sum of longest segments for a given set of leaf configuration may be one component M1 of the modulability factor M. In the above example, the example of target and critical organ may be represented by the model shown in FIG. 4D. For leaves that are oriented in the left-right direction (like that shown in FIG. 4B), the modulability value for the first row of leaf(s) is 1, since the longest segment of target in the first row of the model has one unit of target "T." Similarly, the modulability values for corresponding rows 2-5 in the model are 1, 1, 1, 1 because each of the rows has one unit of target "T." Thus, the M1 value for the set of leaf configuration shown in FIG. 4B is equal to 1+1+1+1+1, which is equal to 5. On the other hand, for leaves that are oriented in the up-down direction (like that shown in FIG. 4C), the modulability value for the first column of leaf(s) is 3, since the longest segment of target in the first column of the model has three units of target. Similarly, the modulability values for corresponding columns 2-5 in the model are 2, 3, 2, 3, which represent the corresponding of the number of target units in the respective columns. Thus, the M1 value for the set of leaf configuration shown in FIG. 4C is equal to 3+2+3+2+3, which is equal to 13. As illustrated in the above examples, the modulability for the set of leaf configuration shown in FIG. 4C, which has a higher modulability value M1, is better than that shown in FIG. 4B.

In some cases, it may be better if there are more leaves contributing in the modulation. Thus, in some embodiments, the modulability factor M may also reflects the number of leaves contributing in achieving a given modulation. Such concept is illustrated in FIGS. 5A-5D. FIG. 5A, which show an example of a target T next to critical organ C. The critical organ C includes critical region C1, C2 (each of which may be considered a critical organ itself). As shown in FIGS. 5B and 5C, the shape of the target T may be accomplished by having the collimator 22 oriented in the left-right configuration, or in the up-down configuration. However, as shown in FIG. 5C, because each component in the target T may be controlled separately, the configuration of the collimator in FIG. 5C provides a better modulability than that in FIG. 5B.

One way to quantify this is to calculate the number of leaves 204 participating (e.g., by having some target projected to the controlled area). Then the target area for each leaf is calculated, and the target area sizes are sort in ascending order. Then a line is fitted to the sorted order of areas, wherein the line may be represented by the equation Leaf Area (or y)=a*sorted order (or x)+b. If slope a is close to zero, that means the target area is evenly distributed to all of the leaves 204, and the modulability is better. In some embodiments, a component in the modulability could then be M2=1/(a+C), where C is some constant, for example 0.01, which serves as a tuning constant that makes the function less steep. An optimal or good value for C may be found using trial and error techniques. Following the example of FIG. 5A, the configuration of the target and critical organ may be represented by the model shown in FIG. 5D. For leaves that are oriented in the left-right direction (like that shown in FIG. 5C), the target areas for the leaves in corresponding rows 1-4 are 1, 1, 1, 1. Thus, in the line model, y=0*x+1, and M2 would be 1/(0+C)=1/C. On the other hand, for leaves that are oriented in the up-down direction (like that shown in FIG. 5B), the target areas for the leaves in corresponding columns 1-5 are 0, 0, 4, 0, 0. Thus, in the line model y=a*x+b, a would have a much higher value than 0, and M2=1/(a+C) would be smaller than 1/C. As illustrated in the above examples, the modulability for the set of leaf configuration shown in FIG. 5C, which has a higher modulability value, is better than that shown in FIG. 5B. In some embodiments, C is used to limit the scale of the measure so that this factor does not dominate the overall result. For example, for low value of C, M2=1/(0+C) would approach infinity and dominate the result. It should be noted that the measure for the distribution of target area should not be limited to using the line model discussed, and that other measures may be used in other embodiments. In other embodiments, a standard deviation or a modification of the standard deviation could be used as a measure of the distribution of the target area.

In some embodiments, the modulability factor could be determined based on the equation M=M1*M2, where M is the total modulability factor. In other embodiments, the modulability factor may be determined based on the equation M=$w_1$M1*$w_2$M2, wherein $w_1$ and $w_2$ are weighted factors, which may be determined experimentally, e.g., through trial and error. In further embodiments, the modulability factor M does not involve M2, in which cases, M1 itself can be used as the modulability factor M. In further embodiments, the modulability factor M does not involve M1, in which cases, M2 itself can be used as the modulability factor M.

In other embodiments, the modulability factor may be determined by considering a movement of sub-volume projections in an aperture (i.e., a hypothetical aperture to be created by a given collimator configuration). As the radiation device rotates around the target, the projected points from the target to the collimator leaf plane move relative to the set of leaves. If a projected point moves and is behind different leaves at different radiation device positions, it is likely to be more easily modulated (because the components are different from different directions). One way to quantify this is to select evenly spaced points from target, calculate the trajectory in leaf plane for each target as the radiation device is rotated, and calculate the sum of the number of leaves contributing to the points.

In the illustrated embodiments, modulability factors are calculated (e.g., by the processor 54) for different positions of gantry angles. The modulability factors may then used by the processor 54 in an optimization process to determine an overall goodness or desirability for a trajectory. In particular, in some embodiments, a modulability may be calculated for each point/segment, e.g., a row of leaf(s), in a collimator plane (i.e., for a given collimator configuration). Then the values for the points/segments are used to form one modulability value for the whole collimator plane (i.e., for the whole collimator configuration that includes all of the leaves at a given gantry angle/position). For example, the modulability values for the points/segments may be summed (e.g., by adding different M1 values for different rows of leaves), aggregated using weighted values, or aggregated based on other schemes. If the algorithm uses M2, then M2 may be determined for the given collimator configuration, and M1 and M2 values for the given collimator configuration may then be used to form a total M for the given collimator configuration (i.e., the collimator configuration at a certain gantry position). Different modulability values for different collimator configurations, which correspond with different gantry angles/positions, may then be combined (e.g., by summing, aggregating using weighted values, or aggregating based on other schemes) to form a single modulability value for a whole trajectory.

Returning to FIG. 3, next a visibility factor V is determined (Step 304). In some embodiments, the visibility factor represents (and therefore, may be used to measure) how well a ray associated with a collimator configuration reaches a target without traversing a target organ. The visibility factor may be a variable, a value, a matrix, or a function. In some embodiments, the visibility factor V is determined by the processor 54 receiving an input (e.g., from a user or a communication device) regarding the visibility factor V. In other embodiments, the modulability factor V is determined by the processor 54 executing a program that involves initializing and/or using the modulability factor V.

One way to quantify how well a ray associated with a collimator configuration reaches a target without traversing a target organ is to evenly sample the point the radiation ray passes through. In such technique, a sum of critical organ samples is reduced from the sum of sample hitting the target. In particular, the visibility factor V may be obtained by determining an amount of target regions traversed by a ray (e.g., a hypothetical ray), determining an amount of critical regions traversed by the ray, and determining a difference using the determined amount of the target regions and the determine amount of the critical regions. To illustrate such concept, assuming a row of leaf(s) is oriented in the left-right direction for the target and critical organ configuration: TTTCCT. In this example, the amount of target regions traversed by a hypothetical ray is 4 because there are four units of target, and the amount of critical regions traversed by the ray is 2 because there are two units of critical organ. The visibility for the given row of leaf(s) may then be calculated by subtracting 2 from 4, which is equal to 2 in the example. Thus, the visibility factor V may be a function of both the target T and critical organ C.

In some embodiments, each target and critical organ may have different weights applied thereto, wherein the weights may be user defined. For example, the relative priorities of the target T and critical organ C may be represented by assigning target T to have priority value of 120, and critical organ C to have priority value of 40. Following the above example with the target and critical organ configuration of TTTCCT, the visibility is then equal to 120+120+120−40−40+120=400. If desired, the value may be normalized in some embodiments. In other embodiments, instead of all target regions having the same priority value, and all critical organs having the same priority value, different target regions may have different priority values, and/or different critical organ sections may have different priority values.

In some embodiments, a visibility may be calculated for each point/segment, e.g., a row of leaf(s), in a collimator plane (i.e., for a given collimator configuration). Then the values are used to form one visibility value for the whole collimator plane (i.e., for the whole collimator configuration that includes all of the leaves at a given gantry angle/position). For example, the values may be summed, aggregated using weighted values, or aggregated based on other schemes. Different visibility values for different gantry angles/positions may then be combined (e.g., by summing, aggregating using weighted values, or aggregating based on other schemes) to form a single visibility value for a whole trajectory.

After the modulability factor M and the visibility factor V have been determined, the factors M, V are then used to determine one or more geometry parameters (Step 306). In some embodiments, the act of determining the geometry parameter(s) may involve determining an objective function f(V,M). For example, V and M can be expressed in terms of the geometry parameter(s), e.g., machine parameter(s), that is desired to be optimized. As illustrated in the above examples, the modulability factor M may depend on the orientation (e.g., rotation about an axis in the direction of the beam) of the collimator 22 with respect to the shape of the target and critical organ (wherein the shape in turns depends on the gantry angle and the maximum size of radiation beam), and the visibility factor V may depend on the direction and maximum size of radiation beam. The optimization may then be performed, e.g., to maximize f, to obtain the geometry parameter(s) that is desired to be determined. In some embodiments, the condition that M and/or V be maximized, or that M and/or V be required to be at least above a prescribed value(s), may be imposed when performing the optimization. Standard optimization technique may be used to perform optimization on the function f. In some embodiments, f can be determined based on the equation f=V*M. In other embodiments, f may be based on the equation $f=k_1 V * k_2 M$, wherein $k_1$ and $k_2$ are weighting factors, which may be determined experimentally (e.g., through trial and error). In further embodiments, f can be determined based on other equations that involve V and M. One optimization method that can be used is the simplex method. First a simplex is formed by calculating a set of initial points with some machine parameters. Then the worst point is replaced by a new point by using the simplex scheme, and the process is repeated until the solution converges. Simplex method for optimization is well known in art, and therefore, it will not be described in further detail. In other embodiments, other optimization techniques that are known in the art may be used to perform optimization of the function f. It should be noted that the objective function f is not limited to having only M and V, and that in other embodiments, the objective function f may include other parameters that are desired to be optimized. Techniques for optimizing parameters using objective function in radiation treatment planning are well known, and therefore, will not described in further detail.

In other embodiments, instead of performing an optimization on the objective function f to determine the geometry parameters, value(s) of the geometry parameter(s) desired to be obtained are first estimated. Then the modulability factor M and the visibility factor V are determined using the estimated value(s) of the geometry parameter(s), and the estimated value(s) of the geometry parameter(s) can then be improved based on the determined factors M, V.

In the illustrated embodiments, the act of determining the geometry parameter(s) is performed using the processor 54.

For example, the processor 54 may be configured (programmed and/or built) to receive information regarding the modulability factor M and the visibility factor V, and perform the optimization of the objective function f using the information. In some embodiments, the processor 54 also provides a user interface for allowing the user to prescribe criteria and input data for use in the optimization process. For example, in some embodiments, the processor 54 may generate a graphical display in the screen, which allows a user to input criteria (e.g., maximum dose, minimum dose, etc.) and information (e.g., target geometry, critical organ geometry, gantry position, etc.) for use in the method 300. In other embodiments, instead of or in addition to the processor 54, the method 300 (or at least part of the method 300) and/or the act of providing the user interface, may be performed by one or more other processor(s). As used in this specification, the term "processor" is not limited to a single processing unit, and may refer to one or more processing units.

After the geometry parameter(s) has been determined, the geometry parameter(s) may be saved in a medium for later use. In some embodiments, the determined geometry parameter(s) may be saved as a part of a treatment plan. In such cases, during a treatment procedure, the geometry parameter(s) may be retrieved for use during treatment. In some embodiments, the determined geometry parameter(s) may be used by the system 10, or another system, to perform a treatment procedure on the patient. In other embodiments, instead of determining geometry parameter(s) for treatment planning and treatment, the method 300 may be used to determine geometry parameter(s) for testing and simulation purposes.

In any of the embodiments described herein, the processor 54 may be configured to consider different possible leaf positions during the optimization process. Consider the following example, which shows indices 0-9 representing different possible leaf positions for a given leaf or leaf pair at a certain gantry position. The corresponding V values for the leaf configurations are also shown.

| Index | Target-Critical Organ | V |
|---|---|---|
| 0 | TTTTT | 5 |
| 1 | TTTCC | 1 |
| 2 | TTTCC | 1 |
| 3 | CCCCC | −5 |
| 4 | TTTCC | 1 |
| 5 | TTTCC | 1 |
| 6 | CCCCC | −5 |
| 7 | TTTTC | 3 |
| 8 | TTTTC | 3 |
| 9 | TTTTC | 4 |

The index refers to different possible spatial locations the leaf (or the row of leaves) could be in, and so the different V values are for different leaf positions for a given leaf (or a row of leaves). In some embodiments, the best continuous sequence of open leaf positions is used. One way to determine the best sequence is to determine the largest sum of V values (calculated over position indices). Each leaf (or leaf pair) can move within a line in the leaf plane. The pair of leaves can form one continuous open area that lets the radiation pass through. The goal is to find the best possible interval that could be open for each leaf/leaf pair and use those regions for each direction to evaluate value of that entry direction (and collimator rotation, which affects the rotation of leaf direction in the leaf plane). Since in some cases, leaf movements are desired to be continuous, the time steps close to each other should be chosen, which correspond to leaf position indices that are close to each other. In the above example, the best interval is from positions 7 to 9, because the sum of V values is 10. This may be used instead of the longest continuous target segment size (which is 5 in interval 0).

In any of the embodiments described herein, the optimization in step 306 may be performed based on fuzzy logic. For example, in some cases, critical organ sparing may be considered when determining a desired modulation. Consider the following example, which shows indices 0-8 representing different possible leaf positions for a given leaf or leaf pair at a certain gantry position. The corresponding V values for the leaf configurations are also shown.

| Index | V |
|---|---|
| 0 | 10 |
| 1 | 10 |
| 2 | −1 |
| 3 | 5 |
| 4 | −10 |
| 5 | 10 |
| 6 | 10 |
| 7 | 1 |
| 8 | −10 |

In the above example, the interval [5, 7] has sum equal to 21, and it is the longest continuous positive segment. However, interval [0, 3] has sum equal to 24 (10+10−1+5). It includes an interval (interval 2) that may have no target, or may have critical organ units that are more than target units. However, extending the interval a bit has more gain (+5) in index 3 than is lost by including index 2 (only −1). Thus, to maximize modulation, interval [0, 3] may be selected. Here, the critical organ sparing is considered in the negative component(s) while trying to maximize modulation. Thus, the desired modulation may be determined based on a selection of the best sub-region, which may be determined by balancing critical organ sparing with target radiation. As illustrated in the above example, in some embodiments, the processor 54 may be configured to consider the incremental effect on the overall modulability M and visibility V (and therefore, the objective function f, and the geometry parameter(s)) resulted from including one or more interval(s).

In some embodiments, the above described embodiments of method 300 may be used to provide some, but not all, of the geometry data required to perform a treatment. In such cases, the method 300 is used to obtain only some geometry parameters, such as isocenter position and/or rotation axis, and another optimization would be required to more accurately produce the treatment and the rest of the treatment machine parameters. In some embodiments, the machine modeling for dose calculation and the dose calculation model in the method 300 may not reflect the actual machine limitation (e.g., they may assume infinite number of leaves and/or infinite speed of leaves), and may be very approximate.

Although the above embodiments have been described with reference to delivering treatment radiation that is in the form of x-rays, in other embodiments, the system and technique described herein may be used for other types of treatment energy. For examples, in other embodiments, in other embodiments, the radiation source 20 may be a proton source for delivering protons to treat a patient, or an electron source for delivering electrons. Accordingly, embodiments of the treatment planning technique described herein may be used to determine treatment plan for other types of treatment, such as proton treatment. Also, it should be noted that the term "collimator" is not limited to a device having leaves for blocking radiation, and may refer to a device having one or more jaws or jaw blocks. Thus, a position of a collimator may refer to position of leaves of a collimator, position of collimator jaws, or a global position of the collimator itself relative to some coordinate system (e.g., a position of the collimator relative to a gantry or relative to a radiation machine, etc.).

In the above embodiments, the method 300 has been described with reference to the radiation source 20 rotating about the target, as in an arc therapy. However, it should be understood that the method 300 is not limited to the example illustrated, and that the method 300 may be used to determine geometry parameter(s) with a different treatment or diagnostic setup. For example, in other embodiments, the radiation source 20 may be configured to translate, instead of rotating, relative to the target. In other embodiments, the patient support 14 may be configured to position the patient in different degrees of freedom, thereby providing different trajectories for delivering radiation towards the target T.

Also, it should be noted that the parameters that can be determined using the method 300 are not limited to the example discussed, and that in other embodiments, the method 300 can be used to determine other parameter(s), such as treatment parameter(s), including and not limited to one or more of a target fluence, a dose, a dose rate, a gantry position, a gantry speed, positions of leaves (i.e., collimator configuration), a beam energy, a beam-on condition, and a beam-off condition. Such parameters may be included in the objective function f, in which case, the optimization of the function f may be performed to determine these parameters.

Although the above embodiments of the method 300 have been described with reference to determining geometry parameter(s) using both the modulability factor M and the visibility factor V, in other embodiments, the geometry parameter(s) may be determined without either the modulability factor M or the visibility factor V. For example, in other embodiments, the method 300 does not include the step 302, in which case, the act 306 of determining the geometry parameter(s) involve using the visibility factor V (e.g., optimizing an objective function f(V) that does not include M). In other embodiments, the method 300 does not include the step 304, in which case, the act 306 of determining the geometry parameter(s) involve using the modulability factor M (e.g., optimizing an objective function f(M) that does not include V).

Computer System Architecture

Figure 6:
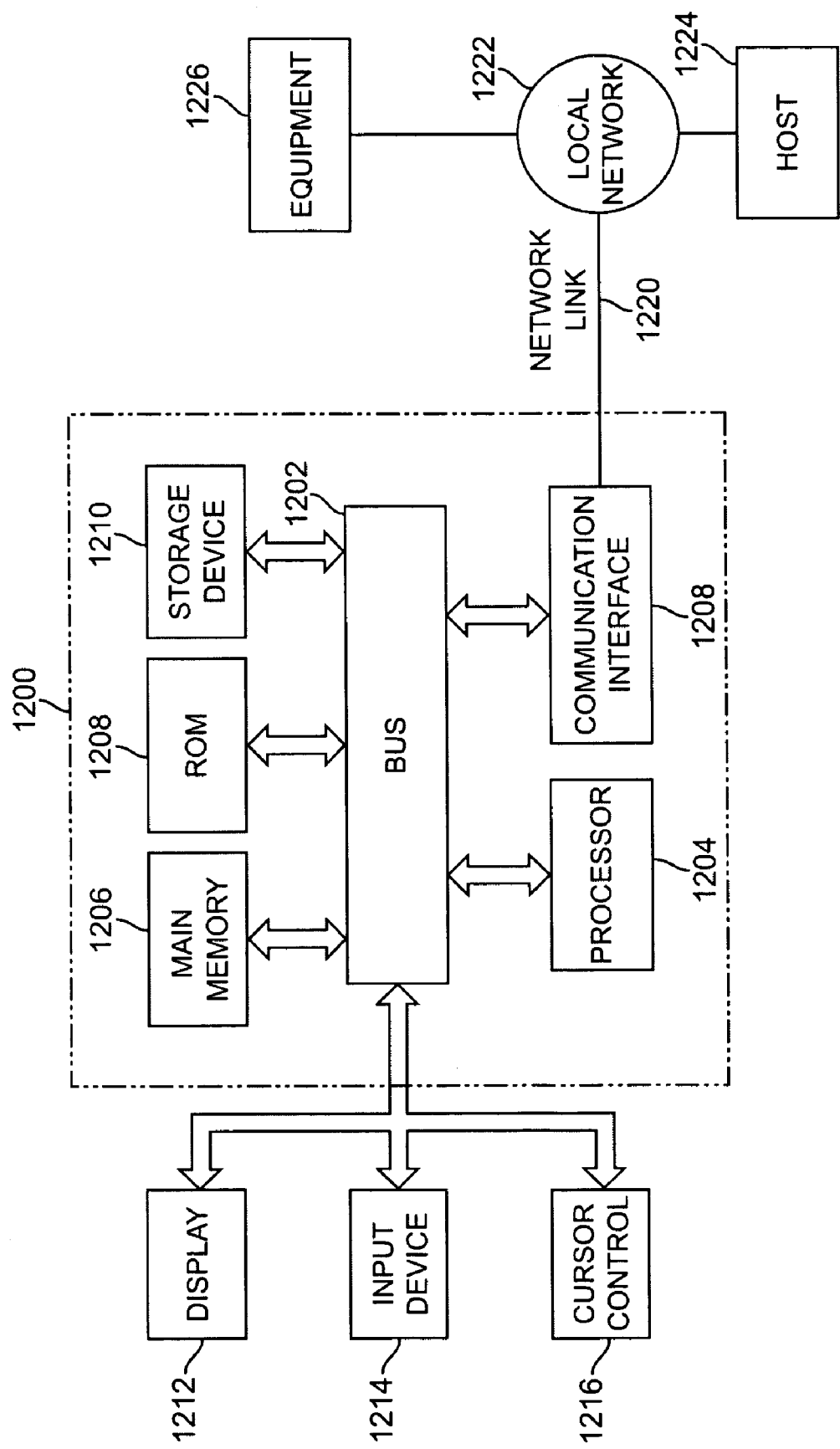
FIG. 6 is a block diagram of a computer system architecture, with which embodiments described herein may be implemented.

FIG. 6 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT) or a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Volatile media includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method for use in a treatment planning process, comprising:
   determining a modulability factor, wherein the modulability factor is a measure of a collimator's ability to modulate its leaves to achieve a given shape for a target;
   determining a treatment parameter by a processor using the modulability factor; and
   storing the treatment parameter in a medium.

2. The method of claim 1, wherein the modulability factor is determined by considering a movement of sub-volume projections in an aperture.

3. The method of claim 1, wherein the modulability factor is a function of a number of leaves participating to form a shape of a fluence.

4. The method of claim 1, wherein the modulability factor is a function of a geometry of the target and a geometry of a critical organ.

5. The method of claim 1, further comprising determining a visibility factor, wherein the treatment parameter is determined using also the visibility factor.

6. The method of claim 5, wherein the visibility factor is a measure of how well a ray associated with a collimator configuration reaches the target without traversing a critical organ.

7. The method of claim 5, wherein the visibility factor is a function of a geometry of the target and a geometry of a critical organ.

8. The method of claim 1, wherein the act of determining the treatment parameter comprises determining an objective function that is a function of the modulability factor and a visibility factor.

9. The method of claim 8, wherein the act of determining the treatment parameter further comprises performing an optimization using the objective function.

10. The method of claim 1, wherein the treatment parameter represents one or more of an isocenter position, a rotation axis, a collimator position, a patient support position, a target fluence, a dose, a dose rate, a gantry position, a gantry speed, a leaf sequence, a beam energy, a beam-on condition, and a beam-off condition.

11. The method of claim 10, wherein the act of determining the modubility factor is performed using the processor.

12. The method of claim 1, wherein the medium comprises a non-transitory medium.

13. A method for use in a treatment planning process, comprising:
    determining a modulability factor;
    determining a treatment parameter using the modulability factor; and
    storing the treatment parameter in a medium;
    wherein the act of determining the modulability factor comprises determining a longest target segment for a leaf of a collimator.

14. The method of claim 13, wherein the act of determining the modulability factor further comprises determining a number of leaves participating to form a shape of a fluence.

15. The method of claim 14, wherein the longest segment for the leaf is used to determine a first factor M1, and the number of leaves participating to form the shape of the fluence is used to determine a second factor M2, and wherein the modulability factor is determined using M1 and M2.

16. A method for use in a treatment planning process, comprising:
    determining a modulability factor;
    determining a treatment parameter using the modulability factor;
    storing the treatment parameter in a medium; and
    determining a visibility factor, wherein the treatment parameter is determined using also the visibility factor;
    wherein the visibility factor is determined by:
      determining an amount of target regions traversed by a ray;
      determining an amount of critical regions traversed by the ray; and
      determining a difference using the determined amount of the target regions and the determined amount of the critical regions.

17. A system for use in a treatment planning process, comprising a processor, wherein the processor is configured for:
    determining a modulability factor, wherein the modulability factor is a measure of a collimator's ability to modulate its leaves to achieve a given shape for a target; and
    determining a treatment parameter using the modulability factor.

18. The system of claim 17, wherein the modulability factor is determined by considering a movement of sub-volume projections in an aperture.

19. The system of claim 17, wherein the modulability factor is a function of a number of leaves participating to form a shape of a fluence.

20. The system of claim 17, wherein the modulability factor is a function of a geometry of the target and a geometry of a critical organ.

21. The system of claim 17, wherein the processor is further configured for determining a visibility factor, and wherein the processor is configured to determine the treatment parameter using also the visibility factor.

22. The system of claim 21, wherein the visibility factor is a measure of how well a ray associated with a collimator configuration reaches the target without traversing a critical organ.

23. The system of claim 21, wherein the visibility factor is a function of a geometry of the target and a geometry of a critical organ.

24. The system of claim 21, wherein the processor is configured to determine the visibility factor by:
   determining an amount of target regions traversed by a ray;
   determining an amount of critical regions traversed by the ray; and
   determining a difference using the determined amount of the target regions and the determined amount of the critical regions.

25. The system of claim 17, wherein the processor is configured for determining the treatment parameter by determining an objective function that is a function of the modulability factor and a visibility factor.

26. The system of claim 25, wherein the processor is configured for determining the treatment parameter by performing an optimization using the objective function.

27. The system of claim 17, wherein the treatment parameter represents one or more of an isocenter position, a rotation axis, a collimator position, a patient support position, a target fluence, a dose, a dose rate, a gantry position, a gantry speed, a leaf sequence, a beam energy, a beam-on condition, and a beam-off condition.

28. A system for use in a treatment planning process, comprising a processor, wherein the processor is configured for:
   determining a modulability factor; and
   determining a treatment parameter using the modulability factor;
   wherein the processor is configured for determining the modulability factor by determining a longest segment for a leaf of a collimator.

29. The system of claim 28, wherein the processor is configured for determining the modulability factor by determining a number of leaves participating to form a shape of a fluence.

30. The system of claim 29, wherein the processor is configured to use longest segment for the leaf to determine a first factor M1, and use the number of leaves participating to form the shape of the fluence to determine a second factor M2, and wherein the processor is configured for determining the modulability factor using M1 and M2.

31. A method for use in a treatment planning process, comprising:
   determining a visibility factor, wherein the visibility factor is a measure of how well a ray associated with a collimator configuration reaches a target without traversing a critical organ;
   determining a treatment parameter by a processor using the visibility factor; and
   storing the treatment parameter in a medium.

32. The method of claim 31, wherein the visibility factor is a function of a geometry of the target and a geometry of the critical organ.

33. The method of claim 31, wherein the act of determining the visibility factor and the act of determining the treatment parameter are performed using a processor.

34. The method of claim 31, wherein the medium comprises a non-transitory medium.

35. A method for use in a treatment planning process, comprising:
   determining a visibility factor;
   determining a treatment parameter using the visibility factor; and
   storing the treatment parameter in a medium;
   wherein the visibility factor is determined by:
      determining an amount of target regions traversed by a ray;
      determining an amount of critical regions traversed by the ray; and
      determining a difference using the determined amount of the target regions and the determined amount of the critical regions.

36. A system for use in a treatment planning process, comprising a processor, wherein the processor is configured for:
   determining a visibility factor, wherein the visibility factor is a measure of how well a ray associated with a collimator configuration reaches a target without traversing a critical organ; and
   determining a treatment parameter using the visibility factor.

37. The system of claim 36, wherein the visibility factor is a function of a geometry of the target and a geometry of the critical organ.

38. A system for use in a treatment planning process, comprising a processor, wherein the processor is configured for:
   determining a visibility factor; and
   determining a treatment parameter using the visibility factor;
   wherein the processor is configured for determining the visibility factor by:
      determining an amount of target regions traversed by a ray;
      determining an amount of critical regions traversed by the ray; and
      determining a difference using the determined amount of the target regions and the determined amount of the critical regions.

* * * * *